United States Patent [19]

Yang et al.

[11] Patent Number: 5,373,081
[45] Date of Patent: Dec. 13, 1994

[54] POLYETHER KETONES AND POLYETHER SULFONES BASED ON PHENYLINDANE, AND THE USE THEREOF FOR OPTICAL SYSTEMS

[75] Inventors: Dazhong Yang, Bayreuth; Gerhard Maier; Oskar Nuyken, both of München; Michael-Joachim Brekner, Frankfurt am Main; Freddy Helmer-Metzmann, Mainz, all of Germany

[73] Assignee: Hoechst Aktiengesellschaft, Frankfurt am Main, Germany

[21] Appl. No.: 21,894

[22] Filed: Feb. 24, 1993

[30] Foreign Application Priority Data

Feb. 26, 1992 [DE] Germany ............... 4205811

[51] Int. Cl.$^5$ ............... C08G 8/02; C08G 14/00
[52] U.S. Cl. ............... 528/125; 528/126; 528/128; 528/174; 528/219; 528/220
[58] Field of Search ............... 528/125, 126, 128, 174, 528/219, 220

[56] References Cited

U.S. PATENT DOCUMENTS

| | | | |
|---|---|---|---|
| 3,065,205 | 11/1962 | Bonner | 528/125 |
| 5,110,893 | 5/1992 | Fukuyama | 528/128 |
| 5,166,304 | 11/1992 | Dübal et al. | 528/128 |

FOREIGN PATENT DOCUMENTS 1387303  3/1975  United Kingdom .
WO90/14378  11/1990  WIPO .

OTHER PUBLICATIONS

Patent Abstracts of Japan, vol. 10, No. 362, (C-389)[2419], published Dec. 4, 1986.

*Primary Examiner*—Morton Foelak
*Assistant Examiner*—P. Hampton-Hightower
*Attorney, Agent, or Firm*—Curtis, Morris & Safford

[57] ABSTRACT

Polyether ketones and polyether sulfones based on phenylindane and the use thereof for optical systems Polymeric ethers containing phenylindane units, of the formula

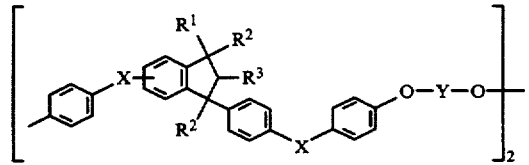

in which
X=CO or SO$_2$,
Y=a divalent heteroarylene radical or an arylene radical or a divalent group of two aryl radicals which are bonded to one another via a bridge,
R$^1$=CH$_3$; R$^2$=R$^3$=H, or
R$^2$=CH$_3$; R$^1$=R$^3$=(C$_1$ to C$_{16}$)-alkyl or aryl, or
R$^1$=CH$_3$; R$^3$=H; R$^2$=(C$_1$ to C$_{16}$)-alkyl or aryl,
are transparent and are suitable for optical systems.

15 Claims, No Drawings

POLYETHER KETONES AND POLYETHER SULFONES BASED ON PHENYLINDANE, AND THE USE THEREOF FOR OPTICAL SYSTEMS

The invention relates to polyaryl ether ketones and polyether sulfones containing phenylindane units, to the preparation thereof, and to the use thereof for optical systems.

Transparent thermoplastics are increasingly being used in optical systems of high-performance optics and in special optics in the form of lenses and prisms, as a support material for various optical coatings, as a transparent coating material on mirrors, lenses and prisms, and as optical waveguides. The general advantage of thermoplastics is their lower processing costs compared with glass, and the low density, which is particularly advantageous for mobile optics. Optical parts made from thermoplastics frequently do not require surface treatments, at high cost, since these materials can be cast or injection-molded in polished molds. Glasses having a refractive index of about 1.5, for example crown glass, are in the same price class as corresponding, transparent thermoplastics. With increasing refractive index, however, glasses become significantly more expensive, and the processing costs and the costs for the surface machining of these glasses, which is always associated with losses of material, also rise. Consequently, replacement of glass by plastic becomes increasingly attractive from an economic point of view with increasing refractive index.

Although the standard plastics employed hitherto for optical applications, such as polymethyl methacrylate and polycarbonate, which have a refractive index of 1.49 and 1.58 respectively, have good processing properties, they also have a relatively low glass transition temperature.

Other amorphous high-performance plastics having a refractive index of from 1.6 to 1.66, such as polyaryl ether sulfones, polyaryl sulfones and polyether-imides, all of which have very high glass transition temperatures ($T_g$ is greater than 180° C.) and are correspondingly more difficult to process, have also been employed in recent years for optical applications (JP-A 61/144,738, JP-A 61/005,986, U.S. Pat. No. 4,477,555, EP-A 0 254 275 and DE-A 34 29 074). The area of polyesters have also seen developments toward amorphous polyesters having a high glass transition temperature, which are likewise suitable for optical applications. The major disadvantage of all amorphous polymers containing ester or amide groups are their low chemical stability and their sensitivity to hydrolysis.

International application WO 90/14378 has already disclosed amorphous, linear, aromatic polyether ketones containing bisoxyphenylindane or bisoxytetramethylspirobiindane units. These polymers were transparent, but exhibited a slight yellow cast.

Proceeding from the property profile covered by the thermoplastics mentioned, the object was to provide a further thermoplastic polymer for optical applications which contains no hydrolysis-sensitive groups, such as ester and amide groups. The absorption of water should be as low as possible. Since the polymer is to be used for optical applications, the transparency should be high and the appearance as colorless as possible. The glass transition temperature should be higher than that of polycarbonate. At the same time, it should be possible to process the polymer at lower temperatures than high-performance polymers such as polyethylimides, and the polymer should have a refractive index comparable to that of polycarbonate and polyether-imides.

Our own studies on various classes of polymer have shown that, surprisingly, certain aromatic polyesters whose chains, in addition to the ether groups, also contain keto groups of sulfonyl groups bonded to phenylindane units, come close to the required property profile.

Commercially available polyaryl ether ketones are partially crystalline. These are polycondensates whose molecules are essentially unbranched and predominantly built up from unsubstituted phenyl or biphenyl units predominantly para-linked to one another via ether or carbonyl groups. They are extremely resistant to solvents and chemical attack and, in the filled state, are distinguished by high heat deformation resistance.

The tendency toward crystallization of such polyaryl ether ketones can be suppressed by disturbing the above-outlined relatively simple, very regular chain structure. For example, incorporation of an increased proportion of ortho- or metalinks of phenyl rings or incorporation of units containing substituted aromatic rings gives amorphous polycondensates. These are soluble in conventional solvents (chloroform, N,N-dimethylacetamide, N,N-dimethylformamide or N-methyl-2-pyrrolidone). They have, in the DSC diagram, only one glass transition temperature and no melting point. From solution and melt, they form solid, flexible and transparent films. By constrast to, for example, the polyaryl ether sulfones, which are likewise amorphous, amorphous polyether ketones have hitherto not attained any industrial significance as thermoplastics.

Use of organic, high-molecular-weight materials having a main chain structure comprising aromatic rings, for example polyether ketones, inter alia, for optical accessory parts for integrated circuits for near-IR radiation is known (JP-A Sho 61/208 001). These parts include lenses, prisms and optical waveguides. However, further details on the composition of the high-molecular-weight materials are not revealed by the publication.

The object was therefore to provide improved polymers which are suitable for optical applications.

The invention therefore relates to polymeric ethers containing phenylindane units built up from at least one structural unit of the formula I $$—O—A—O—Y— \qquad (I)$$

where
A is the 

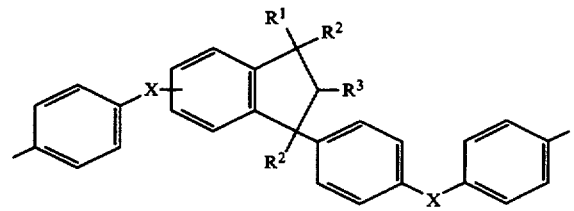

radical
where
X=CO or $SO_2$,
$R^1$=$CH_3$; $R^2$=$R^3$=H or
$R^2$=$CH_3$; $R^1$=$R^3$=($C_1$ to $C_{16}$)-alkyl or aryl,
$R^1$=$CH_3$; $R^3$=H; $R^2$=($C_1$ to $C_{16}$)-alkyl or aryl, and Y is a divalent heteroarylene radical or an arylene radical or a divalent group of two aryl radicals bonded to one another via a bridge.

Examples of a divalent group which comprises two monovalent aryl radicals bonded to one another by a bridge are radicals derived from phenylindane, in particular the

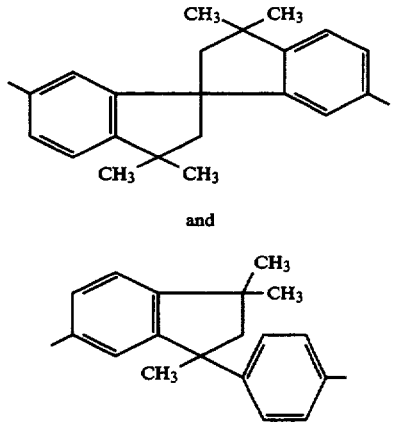

and

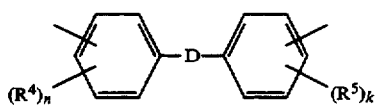

radicals.

Excellent polymers can also be prepared if Y is

in which $R^4$ and $R^5$ are identical or different and are halogen, preferably Cl or Br, $C_1$-$C_4$-alkyl or $C_1$-$C_4$-alkoxy groups or phenoxy groups, k and n are identical or different and are zero or an integer from 1 to 4, and D is a keto group, a terephthaloyl group, a hydrocarbon radical, which may also be substituted by trifluoromethyl groups, a heterocyclic ring or a group comprising sulfur and/or oxygen. The radicals $R^4$ and $R^5$ are preferably in the 3- or 3,5-position with respect to D. If D is a hydrocarbon radical, which may also be substituted by trifluoromethyl groups, D is preferably selected from

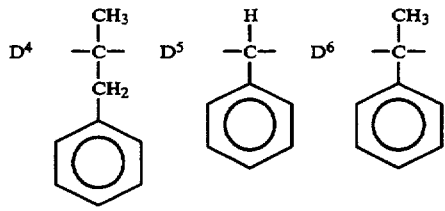

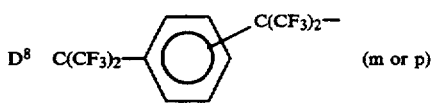

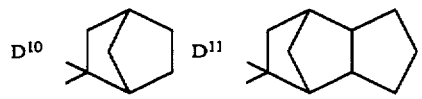

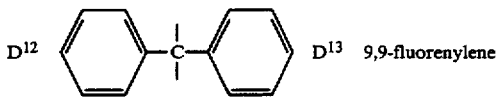

If D is a heterocyclic ring, furylene, oxadiazolylene and thiadiazolylene radicals are preferred.

If D comprises sulfur and/or oxygen, the —S—, —O—, —SO— and —SO$_2$— groups are essentially of interest.

Excellent polymers are also obtained if the radical Y is an arylene radical. In this case, Y can be, for example, a 1,5-, 1,8-, 2,6- or 9,10-antrhacenylene radical, a fluorenylene radical or a 1,5-, 2,6- or 2,7-napththylene radical. The two free valencies may also be present on the same ring in the naphthalene skeleton. Preference is given to the

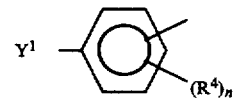

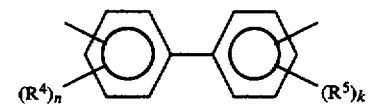

radicals in which $R^4$ and $R^5$ are identical or different and are halogen, preferably Cl or Br, $C_1$-$C_4$-alkyl or $C_1$-$C_4$-alkoxy groups or phenoxy groups, and k and n are identical or different and are zero or an integer from 1 to 4. $R^4$ in the radical $Y^1$ may also be phenyl. k and n are preferably zero, 1 or 2, in particular zero or 2. If $R^4$ and $R^5$ are halogen, k and n are preferably 2. Particular preference is given to the o-, m- and p-phenylene radicals. If Y is a divalent heteroarylene radical, the radicals 2,5-pyridylene, 2,5-furylene, 2,5-oxadiazolylene, 2,5-oxazolylene and 2,5-thiadiazolylene are preferred.

The alkyl radicals $R^1$, $R^2$ and $R^3$ on the phenylindane units A may be linear or branched, monocyclic or polycyclic. They preferably contain 1 to 4 carbon atoms, in particular one carbon atom. It is particularly preferred if $R^1 = R^2 = CH_3$ and $R^3 = H$. The aryl radicals $R^1$, $R^2$ and $R^3$ on the phenylindanes units A are preferably phenyl radicals.

The polymers according to the invention can be prepared by reacting a halogen compound of the formula II

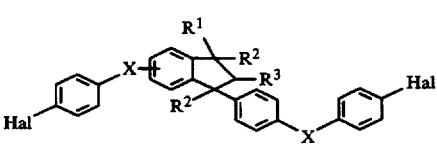

where

Hal is chlorine, fluorine, bromine or iodine,

X is CO or SO$_2$, and

R$^1$, R$^2$ and R$^3$ are as defined above, with the approximately equimolar amount of an aromatic or heteroaromatic dihydroxyl compound HO—Y—OH where Y is as defined above, in an aprotic, dipolar solvent. In this nucleophilic polycondensation, the phenolate ions formed from bisphenol by the action of alkalis are the actual agent (German Patent 15 45 106 and Canadian Patent 847,953) which substitutes the halogen atoms of the compound II which have been activated by groups X in the para-position.

The molar ratio between the monomers (II) and Y(OH)$_2$, which result in the units A and Y, is generally from 0.95 to 1.05:1.0, preferably 1:1. In the case of polymers prepared using dihydroxyindane compounds, this molar ratio is generally from 1.001 to 1.06:1, preferably from 1.002 to 1.05:1, in particular from 1.004 to 1.05:1.

The polymers mentioned may be homopolycondensates, i.e. containing only one unit of type A and one unit of type Y per recurring unit, or copolycondensates, containing two or more different units of type A and/or two or more different units of type Y.

In addition to a homopolycondensate or a copolycondensate, it is also possible to employ polymer mixtures comprising two or more of the abovementioned homopolycondensates, two or more of said copolycondensates or at least one homopolycondensate and at least one copolycondensate.

The polyaryl ether ketones and sulfones (I) employed according to the invention can be used to produce elements for optical systems. The term "elements of optical systems" is taken to mean optical parts of equipment, parts from special optics, including systems from the high-performance optics sector, light propagation and opto-electronics, for example lenses, prisms, illumination and projection systems, light propagation systems, optical coatings and optical substrates.

A prerequisite for a thermoplastic being transparent is the absence of intrinsic absorption in the relevant wavelength range and the absence of refractive-index fluctuations which cause significant scattering losses.

Refractive-index fluctuations are caused either by physical biphasality, i.e. partial crystallinity, or by chemical biphasality, i.e. separation. Impurities can have an adverse effect on the transparency of the material, both as centers of absorption and centers of scattering, but, in contrast to the abovementioned factors, can be eliminated by technological measures relating both to the polymer synthesis and to the polymer processing.

The polymeric ethers according to the invention (where X=CO) can in principle also be built up by electrophilic polycondensation by the Friedel-Crafts method, in which the corresponding phenylindane dicarboxylic acid halides are reacted with the corresponding phenyl ethers of the bishydroxyl compounds Y(OH)$_2$. In accordance with the prior art, various reaction conditions can be selected (cf. U.S. Pat. No. 3,065,205, U.S. Pat. No. 3,441,538, British Patent Application 1,387,303 and WO 84/3 8991).

Examples of suitable aromatic dihydroxyl compounds Y(OH)$_2$ are monocyclic diphenols of the formula

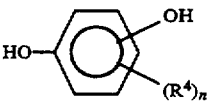
(III)

such as hydroquinone, resorcinol or homologs thereof, such as methylhydroquinone, 2,3- and 2,5-dimethylhydroquinone, 2,3,5,6-tetramethylhydroquinone and 2-methylresorcinol. Preference is given to hydroquinone, resorcinol and 2,3- and 2,5-dimethylhydroquinone. Examples of suitable polycyclic dihydroxyl compounds are those in which two alkyl- or alkoxy-substituted or unsubstituted phenol radicals are linked via a direct bond or via atoms or groups such as alkylidene, oxygen or carbonyl. Some of the suitable compounds may be described by the formula IV

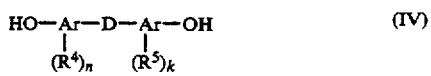
(IV)

where Ar is an aryl radical, preferably phenylene, which may be substituted by R$^4$ and R$^5$ groups. R$^4$ and R$^5$ are halogen, preferably bromine or chlorine, alkyl groups or alkoxy groups, in each case having 1 to 8 carbon atoms, preferably 1 to 4 carbon atoms, or aryl or aryloxy groups (aryl is preferably phenyl). k and n are identical or different and are generally integers from 0 to 4, preferably zero, 1 or 2, in particular zero or 2. D is, for example, an alkylene group, in particular having 1 to 3 carbon atoms, which may be substituted by halogen, preferably fluorine, or by an aryl ring, or is a C$_6$–C$_{10}$-cycloalkylidene group or a direct bond and includes the groups: —O—, —C=O, —CH$_2$—, —C(CH$_3$)$_2$—, —C(CF$_3$)$_2$—,

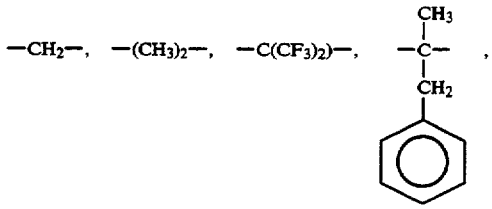

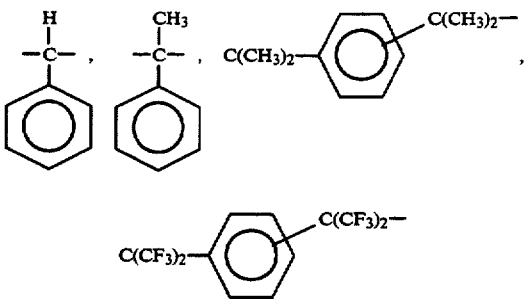

Corresponding compounds IV can be prepared from substituted or unsubstituted phenols and oxo compounds, such as acetone, formaldehyde, cyclohexanone, 2-haptanone, 2-octanone, etc.

Examples of polycyclic dihydroxyl compounds of this type are bis(4-hydroxyphenyl)methane, 3,4'-dihydroxydiphenyl, 4,4'-dihydroxybenzophenone, 4,4'-dihydroxydiphenyl ether, bis(3,5-dimethyl-4-hydroxyphenyl)methane, 2,2-bis(4-hydroxyphenyl)phenylpropane, 1,1-bis(4-hydroxyphenyl)phenylethane, 1,3-bis(4-hydroxyphenylisopropylidene)benzene, 1,3-bis(3,5-dimethyl-4-hydroxyphenylisopropylidene)benzene, 1,3-bis(4-hydroxyphenyl-1,1,1,3,3,3-hexafluoroisopropylidene)benzene, 1,3-bis(3,5-dimethyl-4-hydroxyphenyl-1,1,1,3,3,3-hexafluoroisopropylidene)benzene, 2,7-dihydroxynaphthalene, 2,3-dihydroxynaphthalene, 1,4-dihydroxynaphthalene, 2,7-dihydroxy-9-fluorenone and preferably the compounds 2,2-bis(4-hydroxyphenyl)propane (bisphenol A), 2,2-bis(3,5-dimethyl-4-hydroxyphenyl)propane, 2,2-bis(3,5-dibromo-4-hydroxyphenyl)propane, 2,2-bis(4-hydroxyphenyl)-1,1,1,3,3,3-hexafluoropropane, 3,3'-dihydroxybiphenyl, 4,4'-dihydroxybiphenyl, 3,3',5,5'-tetramethyl-4,4'-dihydroxybiphenyl, 3,3',5,5'-tetramethyl-4,4'-dihydroxybenzophenone, 2,2-bis(3,5-dimethyl-4-hydroxyphenyl)-1,1,1,3,3,3-hexafluoropropane, 1,4-bis(4-hydroxyphenylisopropylidene)benzene, 1,4-bis(3,5-dimethyl-4-hydroxyphenylisopropylidene)benzene, 1,4-bis(4-hydroxyphenyl-1,1,1,3,3,3-hexafluoroisopropylidene)benzene, 1,4-bis(3,5-dimethyl-4-hydroxyphenyl-1,1,1,3,3,3-hexafluoroisopropylidene)benzene, 1,5-dihydroxynaphthalene, 2,6-dihydroxynaphthalene, 5-hydroxy-3-(4-hydroxyphenyl)-1,1,3-trimethylindane, 5-hydroxy-3-(3,5-dimethyl-4-hydroxyphenyl)-1,1,3,4,6-pentamethylindane and 6,6'-dihydroxy-3,3,3',3'-tetramethyl-1,1'-spirobiindane. The preparation of indane-containing bisphenols Y(OH)₂ is described in international application WO 90/14378.

The activated aromatic dihalogen compounds can be obtained from the phenylindane of the formula

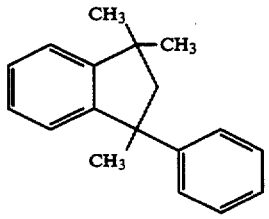

by reaction with an acid halide of the formula Hal-p.C₆H₄-X-Hal¹ in a solvent in the presence of AlCl₃. Hal and Hal¹ here, independently of one another, are chlorine or fluorine, and X is SO₂ or CO. An isomer mixture of the 5- and 6-substituted phenylindanes is formed. The 6-isomer can be obtained in pure form by recrystallization. The pure 6-isomer can also be obtained from the 3-phenylindane-6,4'-di(carboxylic halide) by means of excess halobenzene in the presence of AlCl₃.

The condensation reaction is carried out either in the presence or absence of an inert solvent in which the polymer formed is soluble at the reaction temperature. Examples of suitable solvents are: diphenyl sulfone, N-cyclohexyl-2-pyrrolidone, cyclic aromatic sulfones such as dibenzothiophene S,S-dioxide, or less preferably, benzophenone and cyclic aromatic ketones, such as 9-fluorenone. Solvents of this type are described, inter alia, in DE-A 2 803 873.

Other suitable solvents are N,N-dimethylformamide, N,N-dimethylacetamide and N-methyl-2-pyrrolidone. In this case, a suitable water entrainer (for example toluene) should be added to the reaction mixture.

The reaction temperature is limited at the lower end by the melting point of at least one of the components or of the solvent and at the upper end by the decomposition temperature of the condensation partners or of any solvent used. It is generally between 100° and 400° C., preferably between 150° and 350° C., and depends, inter alia, on the reactivity of the condensation partners and on the type of solvent used. It is preferred to commence with a low reaction temperature and to increase the temperature gradually or in steps when the viscosity of the reaction composition increases.

The inherent viscosity, determined in accordance with DIN 51562, of the polymers according to the invention, as a measure of their molecular weight, measured in a solution of 0.1 g of the polymer in 100 ml of chloroform at 25° C., can be in the broad range from 0.2 to 2.5 dl/g, preferably from 0.3 to 1.5 dl/g.

The transparency of the polymer according to the invention is high and depends, to a certain extent, on the presence of soiling, which may, depending on the preparation method, be in the forte of residual salt or residual solvents. Appropriate purification steps, which may comprise, for example, repeated washing, repeated re-precipitation, but also filtration of the polisher solution or of the polymer melt, improves the transparency of the amorphous polyaryl ether ketones. The transparency or cleanliness of the material can always be assessed in combination with concrete applications. Consequently, use as optical waveguides implies, for example, much more complex purification procedures than does use as a mirror substrate.

The polymers mentioned are amorphous. Their glass transition temperatures, according to DSC measurements (Differential Scanning Calorimetry) at 20° C./min are above 155° C. and thus above the glass transition temperature of polycarbonate. Preference is given to polymers having glass transition temperatures of above 180° C.

The processing temperatures for extrusion are between 230° and 350° C., preferably between 230° and 330° C., particularly preferably between 235° and 320° C.

The densities of the amorphous polyether ketones are generally below those of analogous polyether sulfones. Depending on the chain structure selected, densities of between 1.2 and 1.4 g/cm³ are measured. Preference is given for the values of the density below 1.35 g/cm³.

Conventional assistants, such as stabilizers, UV absorbers, brighteners, mold-release agents and antistatics, can be incorporated without impairment of the properties described.

The high glass transition temperature and the relatively good processing properties result in efficient use of these polymers in the area of high-performance optics, where, particularly in the case of illumination optics and projection optics, ever-higher energy densities are desired today, which then also require higher heat resistance of the optical elements through which light is passed. For example, lenses or diffusion screens made from the polymers according to the invention are superior for such applications to those made from polymethyl methacrylate, polystyrene or polycarbonate.

The injection-moldability of the poisoners according to the invention offers particular advantages in the production of optical elements for special light designs, by means of which both bundled, singly or multiply, and scattered light distribution is simultaneously aimed at. Such optical elements have very complex geometrical shapes whose production in the necessary surface quality and at acceptable cost is possible virtually exclusively from plastics. Local heating in these optical parts, which the poisoners according to the invention survive without difficulty, frequently exceeds the heat resistance of standard transparent plastics.

The area of light propagation over short distances which experience particular heating is another where the thermoplastics according to the invention offer some advantages. In addition to processability by extrusion to give films or fibers, the relatively high refractive index results in very good light bundling and thus in suitability as a core material for optical fibers or films. The films and fibers made from these amorphous polyether ketones can also be employed as waveguides in relatively large thicknesses or diameters. Polyaryl ether ketones having refractive indices of less than 1.65 can also be employed as a cladding material for optical waveguides. Preference Is given to polymers having refractive indices of less than 1.63. Suitable cladding materials for optical waveguides having polymer cores with a very high refractive index are a large number of thermoplastics, for example polyarylates, polysulfones, polyacrylates, polymethacrylates and vinyl polymers. Suitable cladding materials also include plastics having an even higher heat distortion resistance than the polymers according to the invention, for example polyether sulfones, which means that the heat distortion resistance of the waveguide in question with a core made from polyaryl ether ketone is increased still further. It is also possible to produce waveguides in which the cladding and core comprise indane-containing polymers with refractive indices differing by values of more than 0.01. Due to the good adhesion achieved therein between the core and cladding, such waveguides are particularly preferred.

The high refractive index of the amorphous polymers employed according to the invention also offers, very generally, the advantage that thin lenses of high refraction can be produced therefrom. It is also very advantageous to use the thermoplastics according to the invention in the production of achromatic optical systems. Not only the high or variable refractive index, but also the variable Abbe number come into play here. For example, a polyaryl ether ketone having a low Abbe number is preferred for negative lenses and a polyaryl ether ketone having a high Abbe number is preferred for positive lenses. The Abbe number denotes the dispersion of an optical medium and is defined as $$v = \frac{n_D - 1}{n_F - n_C}$$

in which $n_D$, $n_F$ and $n_C$ are the refractive indices of the medium at the helium D line and at the Fraunhofer F and C lines respectively. Its value depends on the elements making up the polymer chain and is in the range from 18 to 40, preferably from 19 to 32, particularly preferably from 20 to 30. The aspherical lenses made from transparent indane-containing polyether ketones and polyether sulfones used in the production of achromatic optical systems can be produced individually or by direct injection molding of polisher around the glass lens to be corrected.

The transparency, the relatively good processing properties, the increased glass transition temperature and other properties, such as the low water absorption capacity, resistance to hydrolysis and insolubility in nonpolar and low-polarity solvents, such as in aliphatic hydrocarbons, alcohols, in diethyl ether, in acetone, inter alia, makes the poisoners according to the invention suitable for use as substrates for optical coatings. Such substrates are distinguished by the fact that light incident on the optical coating passes through them, that they have favorable surface properties for coating, such as insolubility, high heat distortion resistance and high chemical resistance, and that the transparency of the substrate is not reduced by the coating process. Suitable optical coatings are both organic and inorganic coatings, for example dye coatings, dielectric coatings and metallic coatings. Preference is given to substrates for optical coatings made from amorphous indane-containing polymers in the form of sheets and films, which are used, for example, as substrates for optical data carriers.

The resistance of the amorphous indane-containing polymers to hydrolysis is utilized in optical systems which are used in corrosive media. It is possible to produce both entire optical elements from the thermoplastics according to the invention and to coat certain optical elements made of glass, metal or plastics, such as, for example, mirrors and lenses, which are exposed to a corrosive medium, with indane-containing polyether sulfates or polyether ketones. The coating then fulfills primarily a protective function (glass is also attacked by some, principally acidic media), but can also take on optical functions, such as, for example, modification of the reflectivity of surfaces.

For coating, the polymers according to the invention are stuck on or pressed in the form of films or processed from solution. Solvents which can be used for the preparation of coating solutions of amorphous polymers according to the invention are: N-methyl-2-pyrrolidone, dimethylsulfoxide, N,N-dimethylacetamide and N,N-dimethylformamide. The coating can also be carried out by spin-coating or immersion. The coating is subsequently dried in a stream of air at from 100° to 140° C.

EXAMPLE 1

Poly(oxyphenylene-bismethylmethylene-phenylenoxyphenylene-carbonylphenylene-1,1,3-trimethylindanylene-5-carbonylphenylene)

0.44 mol BFBPI (=4,6-bis(4-fluorobenzoyl)-1,3,3-trimethyl-1-phenylindane) and 0.44 mol of bisphenol A were dissolved in 1.5 l of N,N-dimethylacetamide and 300 ml of toluene in a 2-liter four-necked flask fitted with stirrer, reflux condenser, water separator and internal thermometer, during which the flask was constantly flushed with an inert gas. When dissolution was complete, 62.18 g of anhydrous soda were added, and the mixture was stirred under reflux until water was no longer separated off in the water separator (about 12 hours). The solution was treated under reflux for a further 3 hours, cooled and poured into 10% strength acetic acid solution. The polymeric title compound was washed a number of times with water/methanol and subsequently with acetone and then dried for 12 hours at 140° C. The powder obtained (100.4 g) had an inherent viscosity of 1.02 dl/g (chloroform; 0.1 g/dl; 25° C.) and a $T_g$ of 204.5° C. After melting and solidification, the material is transparent.

EXAMPLE 2

Preparation of intermediates of formula $AF_2$ 20 g (84.6 mmol) of 1,1,3-trimethyl-3-phenylindane are heated at the boil for 12 hours with 27 g (170 mmol)

of 4-fluorobenzoyl chloride in the presence of 29.3 g (220 mmol) of AlI₃ in 100 ml of nitrobenzene as solvent. The solvent is subsequently removed in vacuo, and 500 ml of 10% strength HCl are slowly added to the residue. This mixture is extracted a number of times with a total of 500 ml of chloroform in order to take up the crude product. The organic phase is washed with water, evaporated in vacuo and pre-purified by column chromatography (silica gel, eluant hexane/ethyl acetate 4:1) twice. Recrystallization from ethanol/water (10:1) gives the monomer in satisfactory purity for polymerization.

Yield: 50%, m.p.: 45°–48° C.

This product contains the two isomers below in the ratio 1:1:

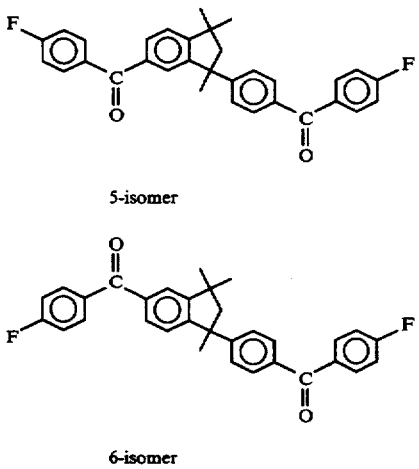

5-isomer 6-isomer

The 5-isomer can be obtained in pure form by recrystallization.

EXAMPLE 3

Preparation of an intermediate

The preparation is carried out entirely analogously to Example 2 from 1,1,3-trimethyl-3-phenylindane and 4-chlorobenzenesulfonyl chloride, but the 5-isomer is obtained in pure form here after only a single recrystallization.

Yield: 35%, m.p.: 200°–202° C.

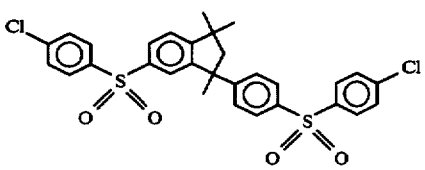

EXAMPLE 4

Preparation of an intermediate

The preparation is carried out entirely analogously to Example 2 from 1,1,3-trimethyl-3-phenylindane and 4-fluorobenzenesulfonyl chloride, but the 5-isomer is obtained in pure form here after only a single recrystallization.

Yield: 35%, m.p.: 168°–170° C.

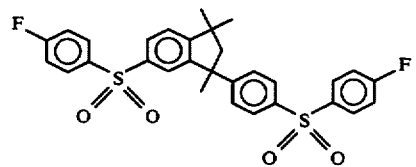

EXAMPLES OF THE POLYMERIZATION

EXAMPLE 5

Poly(oxyphenylene-oxyphenylene-oxyphenylene-carbonylphenylene-1,2,3-trimethylindanylene-carbonylphenylene)

600 mg (1.2 mmol) of the monomer from Example 2 (isomer mixture), 243 mg (1.2 mmol) of 4,4'-dihydroxydiphenyl ether and 249 mg (1.8 mmol) of K₂CO₃ are heated at 190° C. for 20 hours in a mixture of 100 ml of NMP and 50 ml of toluene in a flask fitted with a water separator. The polymer is precipitated by pouring the solution into 500 ml of methanol, and is dissolved in tetrahydrofuran, re-precipitated using methanol, filtered off and dried in vacuo.

Yield: 80%

Molecular weight $M_n=12,000$; $M_w=21,000$ $T_g=193°$ C., $T_d=438°$ C. (commencement of decrease in weight in air, heating rate 10 K/min).

EXAMPLE 6

1.0 g (2.08 mmol) of the monomer from Example 2 (isomer mixture), 387 mg (2.08 mmol) of 4,4'-dihydroxybiphenyl and 431 mg (3.12 mmol) of K₂CO₃ are heated to 190° C. in a mixture of 140 ml of N-methylpyrrolidone (=NMP) and 70 ml of toluene in a flask fitted with a water separator. After 20 hours, the polymer is precipitated by pouring the solution into 500 ml of methanol, and is dissolved in THF, re-precipitated using methanol, filtered off and dried in vacuo.

Yield: 90%

Molecular weight: $M_n=13,500$; $M_w=28,400$ $T_g=219°$ C., $T_g=458°$ C. (commencement of decrease in weight in air, heating rate 10 K/min).

EXAMPLE 7

1.0 g (1.71 mmol) of the monomer from Example 3 (5-isomer), 346 mg (1.71 mmol) of 4,4'-dihydroxydiphenyl ether and 355 mg (2.57 mmol) of K₂CO₃ are heated at 190° C. for 20 hours in a mixture of 140 ml of NMP and 70 ml of toluene in a flask fitted with water separator. The polymer is precipitated by pouring the solution into 500 ml of methanol, and is dissolved in THF, re-precipitated using methanol, filtered off and dried in vacuo.

Yield: 70%

Molecular weight $M_n=16,000$; $M_w=26,000$ $T_g=225°$ C., $T_g=428°$ C. (commencement of decrease in weight in air, heating rate 10 K/min).

The polymers from Examples 5 to 7 are soluble in N-methylpyrrolidone, dimethyl sulfoxide, THF and chloroform at room temperature. DSC measurements (DSC7, Perkin Elmer) indicate the glass transition temperatures stated, but give no indication of partial crystallinity of the polymers. The stated molecular weights were determined by GPC (polystyrene calibration, THF as eluant).

EXAMPLES 8–16

In each case, analogously to Example 1, 0.44 mol of the fluorine component BFBPI were reacted with 0.44 mol of the bishydroxyl component. The structure of the resultant polymers, the refractive index no, their inherent viscosity (measured in $CHCl_3$) and their glass transition temperature $T_g$ are shown in Tables 1 and 2.

EXAMPLE 17

Example 1 was repeated, but the fluorine component (BFBPI) was replaced by 0.44 mol of the corresponding chlorine compound 4,6-bis(4-chlorobenzoyl)-1,3,3-trimethyl-1-phenylindane together with 0.146 mol of KF.

The polymer from Example 1 is formed, having a $T_g$ of 200° C. and an inherent viscosity of 0.36 dl/g (chloroform; 0.1 g/dl; 25° C.).

TABLE 1

| | Inherent viscosity (dl/g) | $T_g$ (°C.) |
|---|---|---|
| Example 8 (n = 1.616) | 0.54 | 210.5 |
| Example 9 (n = 1.614) | 0.37 | 231.0 |
| Example 10 (n = 1.625) | 0.23 | 215.5 |
| Example 11 (n = 1.644) | 0.32 | 187.0 |
| Example 12 (n = 1.627) | 0.65 | 204.5 |

TABLE 2

| | Inherent viscosity (dl/g) | $T_g$ (°C.) |
|---|---|---|
| Example 13 | 0.42 | 171.5 |
| Example 14 (n = 1.639) | 0.31 | 216.0 |
| Example 15 (n = 1.646) | 0.54 | 195.0 |

TABLE 2-continued

| | Inherent viscosity (dl/g) | $T_g$ (°C.) |
|---|---|---|
| 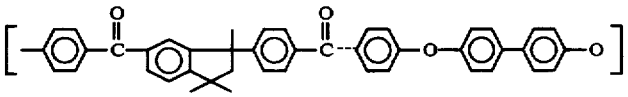 Example 16 (n = 1.659) 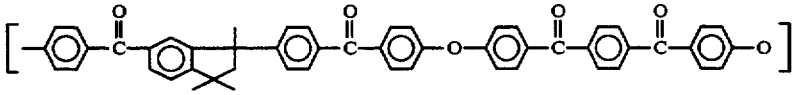 | 0.36 | 190.5 |

We claim:

1. A polymeric ether containing phenylindane units and polar groups, which comprises units of the formula

in which
X = CO or $SO_2$,
Y = a divalent heteroarylene radical or arylene radical or a divalent group of two aryl radicals bonded to one another via a bridge,
$R^1$ = $CH_3$; $R^2$ = $R^3$ = H or
$R^2$ = $CH_3$; $R^1$ = $R^3$ = ($C_1$ to $C_{16}$)-alkyl or aryl, or
$R^1$ = $CH_3$; $R^3$ = H; $R^2$ = ($C_1$ to $C_{16}$)-alkyl or aryl.

2. A polymeric ether as claimed in claim 1, wherein the divalent arylene radical Y is derived from a phenylindane.

3. A polymeric ether as claimed in claim 2, wherein Y is

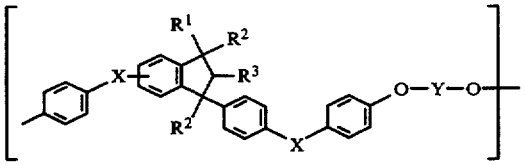

4. A polymeric ether as claimed in claim 2, wherein Y is

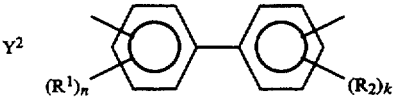

5. A polymeric ether as claimed in claim 1, wherein Y is selected from the radicals:

$Y^1$ 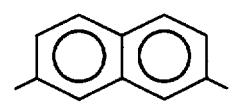

$Y^2$ 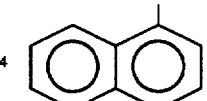

$Y^3$ 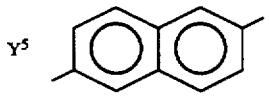  $Y^4$ 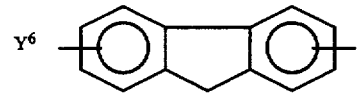

$Y^5$ 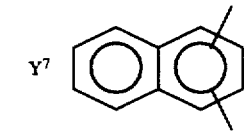

$Y^6$ 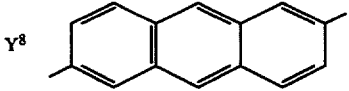

$Y^7$ 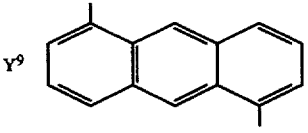

$Y^8$ 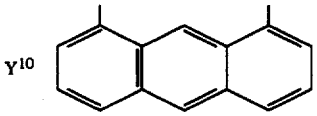

$Y^9$ 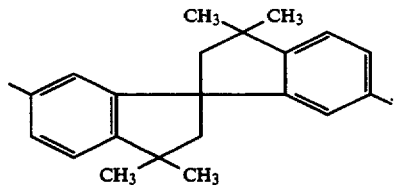

$Y^{10}$ 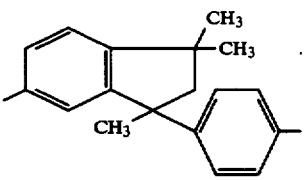

or

17
-continued

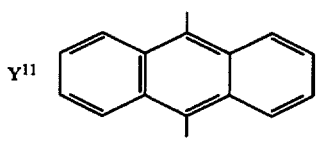

in which R¹ and R² are identical or different and are halogen, $C_1$–$C_4$-alkyl or $C_1$–$C_4$-alkoxy groups or a phenyl group, and k and n are identical or different and are zero or an integer from 1 to 4.

6. A polymeric ether as claimed in claim 1, wherein Y is

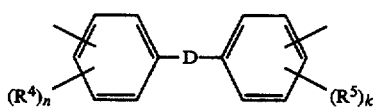

in which R⁴ and R⁵ are identical or different and are halogen, $C_1$–$C_4$-alkyl or $C_1$–$C_4$-alkoxy groups, k and n are identical or different and are zero or an integer from 1 to 4, and D is a keto group or a hydrocarbon radical, which may be substituted by trifluoromethyl groups.

7. A polymeric ether as claimed in claim 6, wherein D is selected from:

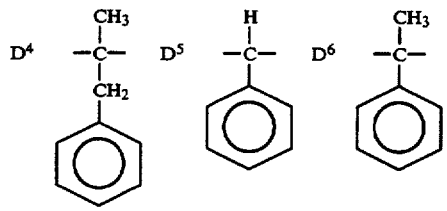

18
-continued

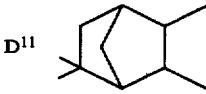 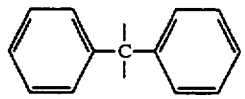

or

D¹³   9,9-fluorenylene.

8. A polymeric ether as claimed in claim 1, where Y is

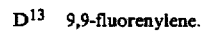

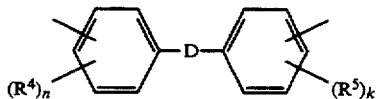

in which R⁴ and R⁵ are identical or different and are halogen, $C_1$–$C_4$-alkyl or $C_1$–$C_4$-alkoxy groups, k and n are identical or different and are zero or an integer from 1 to 4, and D is a heterocyclic ring.

9. A polymeric ether as claimed in claim 8, wherein D is a furylene, oxadiazolylene or thiadiazolylene radical.

10. A polymeric ether as claimed in claim 1, wherein Y is

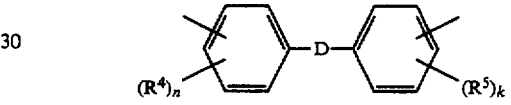

in which R⁴ and R⁵ are identical or different and are halogen, $C_1$–$C_4$-alkyl or $C_1$–$C_4$-alkoxy groups, k and n are identical or different and are zero or an integer from 1 to 4, and D comprises sulfur and/or oxygen.

11. A polymeric ether as claimed in claim 10, wherein D is selected from:

D¹⁵—O—,
D¹⁶—S—,
D¹⁷—SO— and
D¹⁸—SO₂—.

12. A polymeric ether as claimed in claim 1, which comprises units of the formula

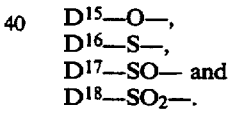

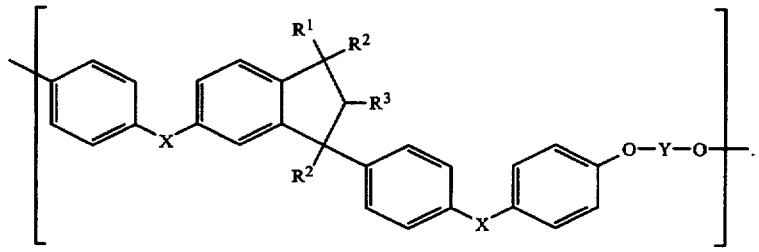

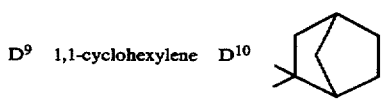

13. A polymeric ether as clawed in claim 1, wherein Y is selected from the divalent heteroarylene radicals 2,5-pyridylene, 2,5-furylene, 2,5-oxadiazolylene, 2,5-thiadiazolylene or 2,5-oxazolylene.

14. A process for the preparation of a polymeric ether as claimed in claim 1, which comprises heating a halogen compound of the formula (II)

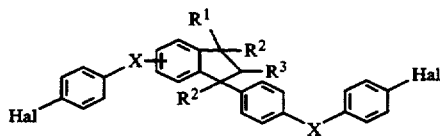
where Hal is chlorine, fluorine, bromine or iodine, and
X, $R^1$, $R^2$ and $R^3$ are as defined in claim 1, with an equimolar amount of an aromatic or heteroaromatic dihydroxyl compound HO—Y—OH where Y is as defined in claim 1, in an aprotic, dipolar solvent.
15. An element for optical systems comprising a polymeric ether as claimed in claim 1.
* * * * *